(12) United States Patent
Hurley et al.

(10) Patent No.: US 8,908,925 B2
(45) Date of Patent: Dec. 9, 2014

(54) METHODS TO BUILD 3D DIGITAL MODELS OF POROUS MEDIA USING A COMBINATION OF HIGH- AND LOW-RESOLUTION DATA AND MULTI-POINT STATISTICS

(75) Inventors: Neil F. Hurley, Boston, MA (US); Tuanfeng Zhang, Lexington, MA (US); Weishu Zhao, Quincy, MA (US); Mustafa Al Ibrahim, Safwa (SA)

(73) Assignee: Schlumberger Technology Corporation, Sugar Land, TX (US)

( * ) Notice: Subject to any disclaimer, the term of this patent is extended or adjusted under 35 U.S.C. 154(b) by 366 days.

(21) Appl. No.: 13/407,526

(22) Filed: Feb. 28, 2012

(65) Prior Publication Data
US 2012/0281883 A1 Nov. 8, 2012

Related U.S. Application Data (60) Provisional application No. 61/447,417, filed on Feb. 28, 2011.

(51) Int. Cl.
G06K 9/00 (2006.01)
G06G 7/50 (2006.01)
G06G 7/48 (2006.01)
G01N 21/64 (2006.01)
E02D 1/00 (2006.01)
E21B 49/00 (2006.01)
E21B 41/00 (2006.01)

(52) U.S. Cl.
CPC .............. *G01N 21/6458* (2013.01); *E02D 1/00* (2013.01); *E21B 49/00* (2013.01); *E21B 41/00* (2013.01)
USPC .................................. 382/109; 703/9; 703/10

(58) Field of Classification Search
None
See application file for complete search history.

(56) References Cited

U.S. PATENT DOCUMENTS

| | | | |
|---|---|---|---|
| 3,013,467 A | 12/1961 | Minsky | |
| 4,107,364 A * | 8/1978 | Sisson | 428/196 |
| 4,702,607 A | 10/1987 | Kinameri | |
| 5,809,163 A * | 9/1998 | Delhomme et al. | 382/109 |
| 6,316,153 B1 | 11/2001 | Goodman et al. | |
| 6,337,568 B1 | 1/2002 | Tutunji et al. | |
| 6,516,080 B1 | 2/2003 | Nur | |
| 6,713,772 B2 | 3/2004 | Goodman et al. | |
| 6,750,974 B2 | 6/2004 | Svetkoff et al. | |
| 6,985,612 B2 * | 1/2006 | Hahn | 382/128 |
| 7,363,160 B2 * | 4/2008 | Seleznev et al. | 702/7 |
| 7,516,055 B2 | 4/2009 | Strebelle | |
| 7,718,351 B2 | 5/2010 | Ying et al. | |

(Continued)

OTHER PUBLICATIONS

Ting Zhang et al."An improved reconstruction model for porous media based on multiple point geostatistics" Apr. 2009 pp. 653-659.*

(Continued)

*Primary Examiner* — Nancy Bitar
(74) *Attorney, Agent, or Firm* — Bridget Laffey; Jakub Michna; Daniel Matthews (57) ABSTRACT

This subject disclosure describes methods to build and/or enhance 3D digital models of porous media by combining high- and low-resolution data to capture large and small pores in single models. High-resolution data includes laser scanning fluorescence microscopy (LSFM), nano computed tomography (CT) scans, and focused ion beam-scanning electron microscopy (FIB-SEM). Low-resolution data includes conventional CT scans, micro computed tomography scans, and synchrotron computed tomography scans.

32 Claims, 8 Drawing Sheets

(56) References Cited

U.S. PATENT DOCUMENTS

| | | | |
|---|---|---|---|
| 7,933,757 | B2 | 4/2011 | Awwiller |
| 8,311,788 | B2 | 11/2012 | Hurley et al. |
| 8,384,017 | B2 | 2/2013 | Botto |
| 2005/0159067 | A1* | 7/2005 | Kunimoto et al. ............ 442/414 |
| 2009/0259446 | A1 | 10/2009 | Zhang et al. |
| 2009/0262603 | A1 | 10/2009 | Hurley et al. |
| 2011/0004447 | A1* | 1/2011 | Hurley et al. ..................... 703/1 |
| 2012/0221306 | A1 | 8/2012 | Hurley et al. |
| 2012/0275658 | A1* | 11/2012 | Hurley et al. ................. 382/109 |
| 2012/0277996 | A1* | 11/2012 | Hurley et al. ................... 702/11 |
| 2012/0281883 | A1* | 11/2012 | Hurley et al. ................. 382/109 |

OTHER PUBLICATIONS

Zhang et al (3D porosity modeling of a carbonate reservoir using continuous multiple point statistics simulation) Sep. 2006.*

Strebelle, Sebastien et al., "Modeling of a Deepwater Turbidite Reservoir Conditional to Seismic Data Using Multiple-Point Geostatistics", Sep. 29-Oct. 2, 2002, SPE Annual Technical Conference and Exhibition, Society of Petroleum Engineers.*

Zhang, "Filter-Based Training Image Pattern Classification for Spatial Pattern Simulation", PhD dissertation, submitted to the Department of Geological and Environmental Sciences, Sanford University, Palo Alto, CA, Mar. 2006, 153 pages.

Zhang et al., "3D Porosity Modeling of a Carbonate Reservoir Using Continuous Multiple-Point Statistics Simulation", presented at the 2005 SPE Annual Conference and Exhibition, Dallas, TX, Oct. 9-12, 2005, SPE Journal, Sep. 2006, pp. 375-379.

International Search Report and Written Opinion of PCT/US2012/027039 on Sep. 12, 2012: pp. 1-9.

Bakke et al., "3-D Pore-Scale Modeling of Sandstones and Flow Simulations in the Pore Networks", SPE 35479, presented at the European 3-D Reservoir Conference held in Stavanger, Norway, Apr. 16-17, 1996, pp. 136-149.

Bear, "Dynamics of Fluids in Porous Media", Elsevier, New York, 1972, pp. 38-57.

Behseresht et al., "Infinite-Acting Physically Representative Networks for Capillarity-Controlled Displacements", SPE 110581, presented at the 2007 SPE Annual Technical Conference and Exhibition held in Anaheim, CA, Nov. 11-14, 2007, pp. 1-15.

Bereskin et al., "Carbonate Microporosity: Recognizing Its Existence and Understanding its Role in Hydrocarbon Production", Producing Low Contrast, Low Resistivity Reservoirs Guidebook, 2009 Rocky Mountain Association of Geologists, Denver, CO, 1996, pp. 33-42.

Bosl et. al., "A Study of Porosity and Permeability Using a Lattice Boltzmann Simulation", Geophysical Research Letters, vol. 25, No. 9, May 1998, pp. 1475-1478.

Bryant et al., "Physically Representative Network Models of Transport in Porous Media", American Institute of Chemical Engineers Journal, vol. 39, No. 3, 1993, pp. 387-396.

Coles et al., "Developments in Synchrotron X-Ray Microtomography with Applications to Flow in Porous Media", SPE 36531, presented at the SPE 1996 Annual Technical Conference and Exhibition held in Denver, CO, Oct. 6-9, 1996, pp. 413-424.

Wikipedia, 2010a, website http://en.wikipedia.org/wiki/Confocal_microscopy, accessed on Oct. 31, 2010; 3 pages.

Creusen et al., "Property Modelling Small Scale Heterogeneity of Carbonate Facies", SPE 111451, presented at the 2007 SPE/EAGE Reservoir Characterization and Simulation Conference held in Abu Dhabi, U.A.E., Oct. 28-31, 2007, pp. 1-5.

Davidson et al., "Investigation of the Petrophysical Properties of a Porous Sandstone Sample Using Confocal Scanning Laser Microscopy", Petroleum Geoscience, vol. 7, No. 2, 2001, pp. 99-105.

Duey, "Quick analysis answers Heidrun questions", Hart Energy Publishing, LP, accessed online at http://www.eandpl.info/index2.php?area=article&articleId=767, Mar. 27, 2008, 4 pages.

Dvorkin et al., "Real Time Monitoring of Permeability, Elastic Moduli and Strength in Sands and Shales Using Digital Rock Physics", SPE 82246, presented at the SPE European Formation Damage Conference held in The Hague, Netherlands, May 13-14, 2003, pp. 1-7.

Nix et al., New Methods Applied to the Microstructure Analysis of Messel Oil Shale: Confocal Laser Scanning Microscopy (CLSM) and Environmental Scanning Electron Microscopy (ESEM), Geology Magazine, 2003, vol. 140 (4), pp. 469-478.

Fredrich, "3D Imaging of Porous Media Using Laser Scanning Confocal Microscopy with Application to Microscale Transport Processes", Physics and Chemistry of the Earth, Part A: Solid Earth and Geodesy, vol. 24, No. 7, 1999, pp. 551-561.

Fredrich et al., "Imaging the Pore Structure of Geomaterials", Science, vol. 268, Apr. 1995, pp. 276-279.

Fredrich et al., "B03201: Predicting Macroscopic Transport Properties Using Microscopic Image Data", Journal of Geophysical Research B: Solid Earth, vol. 111, Issue 3, 2006, pp. 1-14.

Fredrich et al., "Predicting Petrophysical Properties Using 3D Image Data", 2007 AAPG Annual Convention, Long Beach, CA, downloaded at http://www.aapg.org, 1 page.

Guardiano et al., "Multivariate Geostatistics: Beyond Bivariate Moments", Geostatistics—Troia, A. Soares. Dordrecht, Netherlands, Kluwer Academic Publications, vol. 1, 1993, pp. 133-144.

Holt, "Particle vs. Laboratory Modelling of in Situ Compaction", Physics and Chemistry of the Earth, Part A: Solid Earth and Geodsy, vol. 26, No. 1-2, 2001, pp. 89-93.

Huang et al., "Super-Resolution Fluorescence Microscopy", Annual Review of Biochemistry, vol. 78, 2009, pp. 993-1016.

Kayser et al., "Visualizing Internal Rock Structures", Offshore, vol. 64, No. 8, 2004, 2 pages.

Kayser et al., "A Closer Look at Pore Geometry", Oilfield Review, vol. 18, No. 1, Spring 2006, pp. 4-13.

Knackstedt et al., "Digital Core Laboratory: Properties of Reservoir Core Derived from 3D images", SPE 87009, presented at the SPE Asia-Pacific Conference on Integrated Modeling for Asset Management, held in Kuala Lumpur, Malaysia, Mar. 29-30, 2004, 14 pages.

Menendez et al., "Confocal Scanning Laser Microscopy Applied to the Study of Pore and Crack Networks in Rocks", Computers in Geoscience, vol. 27, No. 9, 2001, pp. 1101-1109.

O'Connor et al., "Microscale Flow Modelling in Geologic Materials", Physics and Chemistry of the Earth, Part A: Solid Earth and Geodesy, vol. 24, Issue 7, 1999, pp. 1-6.

Okabe et al., "Prediction of Permeability for Porous Media Reconstructed Using Multiple-Point Statistics", Physical Review E, vol. 70, 2004, 10 pages.

Okabe et al., "Pore Space Reconstruction Using Multiple-Point Statistics", Journal of Petroleum Science and Engineering, vol. 46, 2005, pp. 121-137.

Okabe et al., "Pore Space Reconstruction of Vuggy Carbonates Using Microtomography and Multiple-Point Statistics", Water Resources Research, vol. 43 (12), 2007, 5 pages.

Okabe et al., "Pore-Scale Heterogeneity Assessed by the Lattifce-Boltzmann Method", International Symposium of the Soc. of Core Analysts, Trondheim, Norway, Sep. 12-16, 2006, 7 pages.

Oren et al., "Extending Predictive Capabilities to Network Models", SPE Journal, vol. 3, Dec. 1998, pp. 324-336.

Oren et al., "Process Based Reconstruction of Sandstones and Prediction of Transport Properties", Transport in Porous Media, vol. 46, 2002, pp. 311-343.

Zhang, "Incorporating Geological Conceptual Models and Interpretations into Reservoir Modeling Using Multiple-Point Geostatistics", Earth Science Frontiers, vol. 15, Issue 1, Jan. 2008, pp. 26-35.

Reid et al., "Monterey Formation Porcelanite Reservoirs of the Elk Hills Field, Kern County, California", AAPG Bulletin, vol. 85, No. 1, 2001, pp. 169-189.

Siddiqui et al., "Techniques for Extracting Reliable Density and Porosity Data from Cuttings", SPE 96918, presented at the 2005 SPE Annual Technical Conference and Exhibition held in Dallas, TX, Oct. 9-12, 2005, pp. 1-13.

Siddiqui et al., "Data Visualization Challenges for Displaying Laboratory Core and Flow Data in Three-Dimensions", SPE 106334, presented at the 2005 SPE Technical Symposium of Saudi Arabia, held in Dhahran, Saudi Arabia, May 14-16, 2005, pp. 1-9.

(56) References Cited

OTHER PUBLICATIONS

Strebelle, "Conditional Simulation of Complex Geological Structures Using Multiple-Point Statistics", Mathematical Geology, vol. 34, No. 1, 2002, pp. 1-21.
Suicmez et al., "Pore Network Modeling: A New Technology for SCAL Predictions and Interpretations", Saudi Arabia Oil and Gas, Issue 5, 2008, 7 pages.
Tomutsa et al., "SCA2003-47: Focussed Ion Beam Assisted Three-Dimensional Rock Imaging at Submicron Scale", presented at the International Symposium of the Society of Core Analysts held in Pau, France, Sep. 21-24, 2003, 6 pages.
Tomutsa et al., "Analysis of Chalk Petrophysical Properties by Means of Submicron-Scale Pore Imaging and Modeling", SPE Reservoir Evaluation and Engineering, vol. 10, Jun. 2007, pp. 285-293.
Tsintzouras et al., "Applications of Confocal Macroscope-Microscope Luminescence Imaging to Sediment Cores", New Techniques in Sediment Core Analysis: Geological Society of London, Special Publication 267, 2006, pp. 141-150.
Vahrenkamp et al., "Multi-Scale Heterogeneity Modelling in a Giant Carbonate Field, Northern Oman", GeoArabia, vol. 13, No. 1, 2008, p. 248.
Vinegar, "X-Ray CT and NMR Imaging of Rocks", Journal of Petroleum Technology, Mar. 1986, pp. 257-259.
Wellington et al., "X-Ray Computerized Tomography", Journal of Petroleum Technology, Aug. 1987, pp. 885-898.
Wikipedia, website http://en.wikipedia.org/wiki/Two-photon_excitation_microscopy, accessed on Oct. 23, 2010; 3 pages.
Withjack et al., "The Role of X-Ray Computed Tomography in Core Analysis", SPE 83467, presented at the SPE Western Regional/AAPG Pacific Section Joint Meeting held in Long Beach, CA, May 19-24, 2003, pp. 1-12.
Wu et al., "3D Stochastic Modelling of Heterogeneous Porous Media—Applications to Reservoir Rocks", Transport in Porous Media, vol. 65, 2006, pp. 443-467.
Wu et al., "Validation of Methods for Multi-Scale Pore Space Reconstruction and Their Use in Prediction of Flow Properties of Carbonate", Paper SCA2008-34, presented at the International Symposium of the Society of Core Analysts held in Abu Dhabi, UAE, Oct. 29-Nov. 2, 2008, pp. 1-12.
Zhang et al., "Models and Methods for Determining Transport Properties of Touching-Vug Carbonates", SPE 96027, presented at the 2005 SPE Annual Technical Conference and Exhibition held in Dallas, TX, Oct. 9-12, 2005, 9 pages.
Zhang et al., "Numerical Modeling of Heterogeneous Carbonates and Multi-Scale Dynamics", SPWLA 50th Annual Logging Symposium, The Woodlands, Texas, Jun. 21-24, 2009, pp. 1-12.
Zhang et al., "Pore Scale Study of Flow in Porous Media: Scale Dependency, REV, and Statistical REV", Geophysical Research Letters, vol. 27 (8), Apr. 2000, pp. 1195-1198.

* cited by examiner

METHODS TO BUILD 3D DIGITAL MODELS OF POROUS MEDIA USING A COMBINATION OF HIGH- AND LOW-RESOLUTION DATA AND MULTI-POINT STATISTICS

CROSS-REFERENCE TO RELATED APPLICATIONS

This application claims benefit of U.S. Provisional Patent Application Ser. No. 61/447,417 filed on Feb. 28, 2011, entitled "Methods to Build 3d Digital Models of porous media using a combination of high- and low-resolution data and multi-point statistics."

This application is also related to commonly assigned U.S. patent application entitled "Method to build 3D digital models of porous media using transmitted laser scanning confocal microscopy and multi-point statistics," Ser. No. 12/459,414, filed on Jul. 1, 2009, U.S. patent application entitled "Method to quantify discrete pore shapes, volumes, and surface areas using confocal profilometry," Ser. No. 12/459,454, filed on Jul. 1, 2009, U.S. patent application entitled "Method for characterizing a geological formation traversed by a borehole," Ser. No. 12/384,945, filed Apr. 10, 2009, U.S. patent application entitled "Method to generate numerical pseudocores using borehole images, digital rock samples, and multi-point statistics," Ser. No. 12/384,721, filed Apr. 8, 2009, U.S. patent application entitled "Multiscale digital rock modeling for reservoir simulation," Ser. No. 13/036,770, filed Feb. 28, 2011, U.S. provisional patent application entitled "Method to determine representative element areas and volumes in porous media," Ser. No. 61/447,419, filed Feb. 28, 2011; and U.S. provisional patent application entitled "Methods of using petrographic image analysis to determine capillary pressure in porous media," Ser. No. 61/447,434, filed on Feb. 28, 2011, U.S. patent application entitled "Method to determine representative element areas and volumes in porous media," Ser. No. 13/407,542, filed herewith; and U.S. patent application entitled "Petrographic Image Analysis For Determining Capillary Pressure In Porous Media," Ser. No. 13/407,561, filed herewith. The content of each of the foregoing applications is incorporated herein by reference.

BACKGROUND

Computed tomographic (CT) images are commonly used to visualize rock-pore systems. CTscans are 2-dimensional (2D) cross sections generated by an X-ray source that either rotates around the sample, or the sample rotates within the source beam. Bulk density is computed from X-ray attenuation coefficients, and serial sections are used to construct 3-dimensional (3D) images. Digital models are built from conventional, microCT, nanoCT, and synchrotron CTscans. Resolution, inversely related to sample size, is on the millimeter to micron to sub-micron scale, depending on the device used. Petrophysical calculations, such as porosity and permeability, are strongly influenced by segmentation of pixels into rock vs. pore. Segmentation is especially difficult if a fraction of the pores are smaller than the resolution of the CT acquisition system.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

According to some embodiments, a method of constructing a model of a sample of porous media is described. The method includes: receiving low resolution image data generated using a lower resolution measurement performed on a sample of the porous media; receiving high resolution image data representing characterizations of aspects (such as shape, size and spacing of pores, etc.) of a smaller sample of the porous media, the high resolution data being generated using a higher resolution measurement performed on the smaller sample; and distributing the characterizations of aspects of smaller sample from the high resolution data into the low resolution data thereby generating an enhanced model of the porous media.

According to some embodiments the distributing includes using a multi-point statistical method, such as discrete variable geostatistics, or continuous variable geostatistics. According to some embodiments, the porous media is a hydrocarbon bearing subterranean rock formation. According to some embodiments, prior to the distributing, the low resolution image data is segmented into a binary image, the segmentation being based in part of the characterizations from high resolution measurement.

According to some embodiments, the high resolution image data is generated using one or more measurements such as: laser scanning fluorescent microscopy, scanning electron microscopy, transmission electron microscopy, atomic force microscopy, vertical-scanning interferometry, nanoCTscans, and focused ion beam-scanning electron microscopy, and the low resolution image data is generated using one or more measurements such as: three dimensional micro CT, three dimensional conventional CT and three dimensional synchrotron CT scans, and macro digital photography.

According to some embodiments, a system for constructing a model of a sample of porous media is described. The system includes a processing system adapted and programmed to receive low resolution image data generated using a lower resolution measurement performed on a first sample of the porous media, receive high resolution image data representing characterizations of aspects of a small sample of the porous media, the high resolution data being generated using a higher resolution measurement performed on the small second sample, and to distribute the characterizations of aspects of the small second sample from the high resolution data into the low resolution data thereby generating an enhanced model of the porous media. According to some embodiments, the porous media is a hydrocarbon bearing reservoir rock formation, and the system includes a sampling system adapted to collect a core-sample from the subterranean rock formation.

According to some embodiments a method of segmenting a digital image of porous media is described. The method includes: receiving a low resolution digital image generated using a lower resolution measurement performed on a first sample of the porous media; receiving a high resolution digital image generated using a higher resolution measurement performed on a small second sample of the porous media; identifying macropores from the high resolution digital image; and segmenting the low resolution digital image thereby generating a binary digital image having two possible values for each pixel, the segmenting being based on the identified macropores.

Further features and advantages of the subject disclosure will become more readily apparent from the following detailed description when taken in conjunction with the accompanying drawings.

BRIEF DESCRIPTION OF THE DRAWINGS

The subject disclosure is further described in the detailed description which follows, in reference to the noted plurality of drawings by way of non-limiting examples of embodiments of the subject disclosure, in which like reference numerals represent similar parts throughout the several views of the drawings, and wherein.

DETAILED DESCRIPTION

The particulars shown herein are by way of example and for purposes of illustrative discussion of the embodiments of the subject disclosure only and are presented in the cause of providing what is believed to be the most useful and readily understood description of the principles and conceptual aspects of the subject disclosure. In this regard, no attempt is made to show structural details of the subject disclosure in more detail than is necessary for the fundamental understanding of the subject disclosure, the description taken with the drawings making apparent to those skilled in the art how the several forms of the subject disclosure may be embodied in practice. Further, like reference numbers and designations in the various drawings indicate like elements.

Laser scanning fluorescence microscopy (LSFM) creates images of polished rock chips that are vacuum-pressure impregnated with fluorescing epoxy. The sample lies on a movable stage, and LSFM scans produce an x-y grid of measured light intensities in regularly spaced z-axis planes. The smallest pores, a function of laser wavelength and microscope optics, are about 0.25 microns in size. 3D volumes are about 10-20 microns thick in carbonate rocks, and about 50-250 microns thick in sandstones. Tiled scans cover 10's of $mm^2$ in surface area.

Representative element volumes (REV) and areas (REA) are the smallest volumes and areas, respectively, which can be modeled to yield consistent results, within acceptable limits of variance of the modeled property (in non limiting examples, porosity and permeability). REVs and REAs allow suitably sized samples to be chosen to ensure heterogeneity in porous media is captured.

According to some embodiments, a combination is described of (a) high-resolution 2D or 3D LSFM images, acquired for REA's or REV's in rocks, with (b) CT scans, which capture relatively larger 3D volumes at lower resolution. LSFM scans are used as training images for 2D or 3D multi-point statistics to distribute high-resolution micropores throughout lower-resolution CT scan volumes, which are used as hard data to condition the simulations. The end result is a composite 3D "total porosity" model that captures large and small pores. An advantage of the technique is that high-resolution data helps solve the segmentation problem for CT scan data. Also, although we apply this approach to rocks, the same techniques apply to any porous media scanned at more than one scale of resolution.

Digital Models of Rocks and Pores.

There are many examples of numerical rock models built using techniques including reconstructions made from 2D thin sections or scanning-electron microscope (SEM) images, computer-generated sphere packs, laser scanning fluorescence microscopy, and various types of CT scans (conventional, microCT, nanoCT, and synchrotron-computed microtomography).

CT Scans.

The most common way to visualize pore systems in 3D is from CT scans. Samples for microCT are selected based on whole-core CT scans. Whole-core CT scans provide an overall view of heterogeneity in the cored interval. Based on CT numbers, which are direct indications of core density, sample locations from various areas of core are marked. Samples are then cut using appropriate tools. No special procedure is needed to clean the samples before microCT scans.

Microtomography employs X-rays to acquire cross-sections of a 3D object that can be used to create virtual models. MicroCT scanners are small in design compared to medical scanners, and are ideally suited for imaging smaller objects such as core samples a few millimeters in size. MicroCT scanners are used to obtain exact 3D details about rock morphology by avoiding approximations needed to reconstruct 3D images via process-based or statistical methods. MicroCT scanners achieve a resolution of about 1 to 5 microns. For further analysis, with resolution below the micron range, nanoCT scanners may be used.

Laser Scanning Fluorescence Microscopy.

Laser scanning fluorescence microscopy (LSFM) provides a high-resolution (about 0.25 microns) technique to build 3D digital rock models. Confocal and multiphoton techniques are most common, although the emerging field of super-resolution fluorescence microscopy may provide improved images of rocks and other porous media, down to a few nm to 10's of nm in scale. See "Huang, B., Bates, M., and Zhuang, X., 2009, Super-resolution fluorescence microscopy: Annual Review of Biochemistry, v. 78, p. 993-1016." Such techniques enhance the resolution of fluorescence microscopy using patterned excitation or single molecule localization of fluorescence.

Confocal microscopy, the most common type of LSFM, uses point illumination and a pinhole placed in front of a detector to eliminate out-of-focus light. Because each measurement is a single point, confocal devices perform scans along grids of parallel lines to provide 2D images of sequential planes at specified depths within a sample.

Depth of penetration of LSFM is limited because reflected light is absorbed and scattered by material above the focal plane. Optical sectioning depths in sandstones ranged from 50 to 250 microns. See, "Fredrich, J. T., 1999, 3D imaging of porous media using laser scanning confocal microscopy with application to microscale transport processes: Physics and Chemistry of the Earth, Part A: Solid Earth and Geodesy, v. 24, Issue 7, p. 551-561." In carbonate rocks, scan depths are 10 to 20 microns. Our experiments have successfully imaged depths as great as 500 microns using pore casts of carbonate rocks, where the rock material has been removed with acid. Fortunately, areal coverage is not limited because tiled scans can be made of relatively large areas (10's of mm$^2$) of polished sections of rock.

Multiphoton microscopy uses two-photon excitation to image living tissue to a very high depth, about one millimeter. See "Wikipedia, 2010a, http://en.wikipedia.org/wiki/Confocal_microscopy, website accessed on Oct. 31, 2010." Like confocal microscopy, this technique excites fluorescent dyes injected into rocks. "The principal is based on the idea that two photons of comparably lower energy than needed for one photon excitation can also excite a fluorophore in one quantum event. Each photon carries approximately half the energy necessary to excite the molecule. An excitation results in the subsequent emission of a fluorescence photon, at a higher energy than either of the two excitatory photons." Resolution is diffraction-limited to about 250 nm, similar to confocal microscopy.

Confocal and multiphoton microscopy is widely used in the life sciences and semiconductor industries. Applications in the earth sciences are much less common.

Multi-Point Statistics.

Multi-point (or multiple-point) statistical methods (MPS) are a new family of spatial statistical interpolation algorithms proposed in the 1990s that are used to generate conditional simulations of discrete variable fields, such as geological facies, through training images. See, "Guardiano, F., and Srivastava, R. M. 1993, Multivariate geostatistics: Beyond bivariate moments: Geostatistics-Troia, A. Soares. Dordrecht, Netherlands, Kluwer Academic Publications, v. 1, p. 133-144." MPS is gaining popularity in reservoir modeling because of its ability to generate realistic models that can be constrained by different types of data. Unlike the conventional 2-point or variogram-based geostatistical approaches, MPS uses a training image to quantify the complex depositional patterns believed to exist in studied reservoirs. These training patterns are then reproduced in the final MPS simulations with conditioning to local data collected from the reservoirs. Therefore, MPS allows modelers to use their prior geological interpretations as conceptual models (training images) in the reservoir modeling process, and to evaluate the uncertainty associated with the prior interpretations by the help of using different training images.

In addition to categorical variables, MPS can also be used to deal with continuous variable training images, such as spatial distribution of porosity. Two families of MPS algorithms are available to handle these different types of training images: Snesim for categorical variables, and Filtersim for continuous variables.

Snesim and Filtersim algorithms honor absolute, or "hard" constraints from data acquired in wells or outcrops, and other interpreted trend maps of the reservoir under study. Training images are the main driver of any MPS approach. An issue raised implicitly by current MPS algorithms is how to generate training images. Training images are designed to model or reproduce real geological features and should as much as possible be derived from existing geologically meaningful images. Training images can be derived from various sources, such as hand-drawn sketches, aerial photographs, satellite images, seismic volumes, geological object-based models, physical-scale models, or geological process-based models.

Categorical variable training images are easier to generate than continuous variable training images. An object-based approach is commonly used to generate training images with categorical variables. A region-based approach, combined with the addition of desired constraints, can be used to generate continuous variable training images. See Zhang T., Bombarde, S., Strebelle, S., and Oatney, E., 2006, 3D porosity modeling of a carbonate reservoir using continuous multiple-point statistics simulation: SPE Journal v. 11, p. 375-379.

Representative Element Areas and Volumes.

Representative element volumes (REV) provide a new way to deal with heterogeneity and upscaling issues in reservoir modeling. In summary, REV is the smallest volume that can be modeled to yield consistent results, within acceptable limits of variance of a modeled property, such as porosity. Using this approach, we can upscale rock properties from fine to coarse scales by determining the smallest volume that needs to be modeled, running the flow model and using the results in larger-scale simulations. Once we have modeled an REV, we do not need to model larger volumes because we have captured heterogeneity for the particular rock type at that scale.

Figure 3:
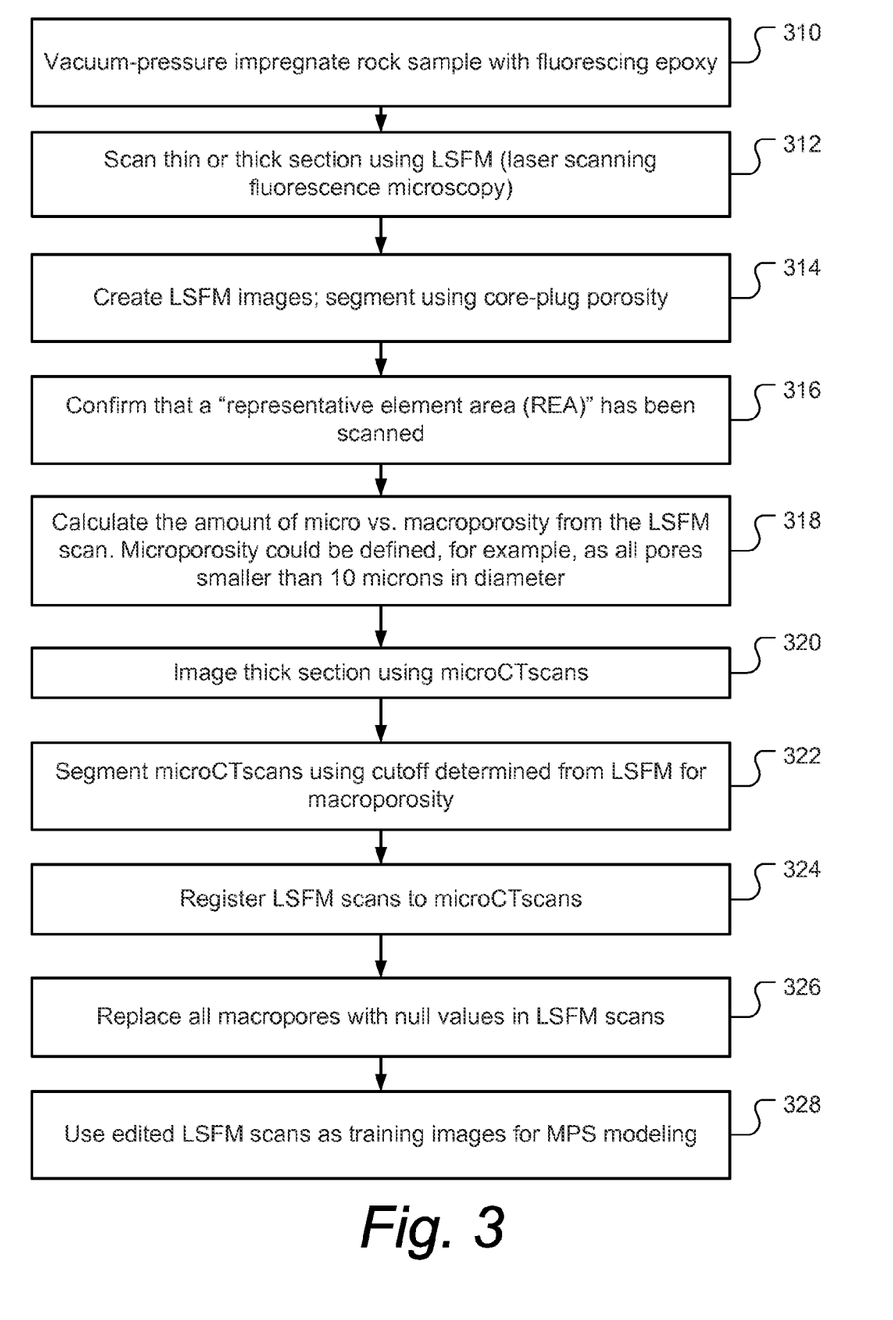
FIG. 3 is a flow chart for composite 2D model using laser scanning fluorescence microscopy (LSFM), microCT scans, multi-point statistics (MPS), and representative element areas (REA's), according to some embodiments.

The concept of REV was first discussed in 1972. See "Bear, J., 1972, Dynamics of fluids in porous media: Elsevier, N.Y., 746 p" (hereinafter "Bear 1972"). Bear defined $\Delta U_i$ as a volume in a porous media, with a centroid of P (FIG. 3). $\Delta U_i$ is considered to be much larger than a single pore or grain. $\Delta U_v$ is the volume of void space, and $n_i$ is the ratio of void space to volume, i.e., the fractional porosity. At large values of $\Delta U_i$, there are minimal fluctuations of porosity as a function of volume. However, as volume decreases, fluctuations in porosity increase, especially as $\Delta U_i$ approaches the size of a single pore, which has fractional porosity of 1. If the centroid P happens to lie in a grain, porosity is 0 when $\Delta U_i$=0. The value $\Delta U_o$ is defined as the REV, below which fluctuations of porosity are significant, and above which fluctuations of porosity are minimal. In brief, the dimensions of $\Delta U_o$ are sufficient so that "the effect of adding or subtracting one or several pores has no influence on the value of n."

Using the REV approach, the porous medium is replaced by "a fictitious continuum: a structureless substance, to any point of which we can assign kinematic and dynamic variables and parameters that are continuous functions of the spatial coordinates of the point and of time" (Bear, 1972). Note that the REV for porosity may differ from the REV for permeability or other parameters. Also, the REV for static vs. dynamic properties may vary. In practice, the best method is to use the largest REV determined for various parameters.

In 2D, the analogous term to REV is representative element area (REA). REA is the smallest area of a rock that is representative of the measured rock property. REA and REV measure area and volume, respectively. Both terms allow us to capture heterogeneity in rock properties.

REA and REV are both determined using an iterative process, whereby variance in a given parameter, such as porosity or permeability, is measured for successively larger sample areas or volumes. REA and REV are determined as the area or volume, respectively, where standard deviation of the variance from the sample mean falls below an acceptable cutoff. Sample mean could be laboratory-derived core-analysis porosity.

Figure 1:
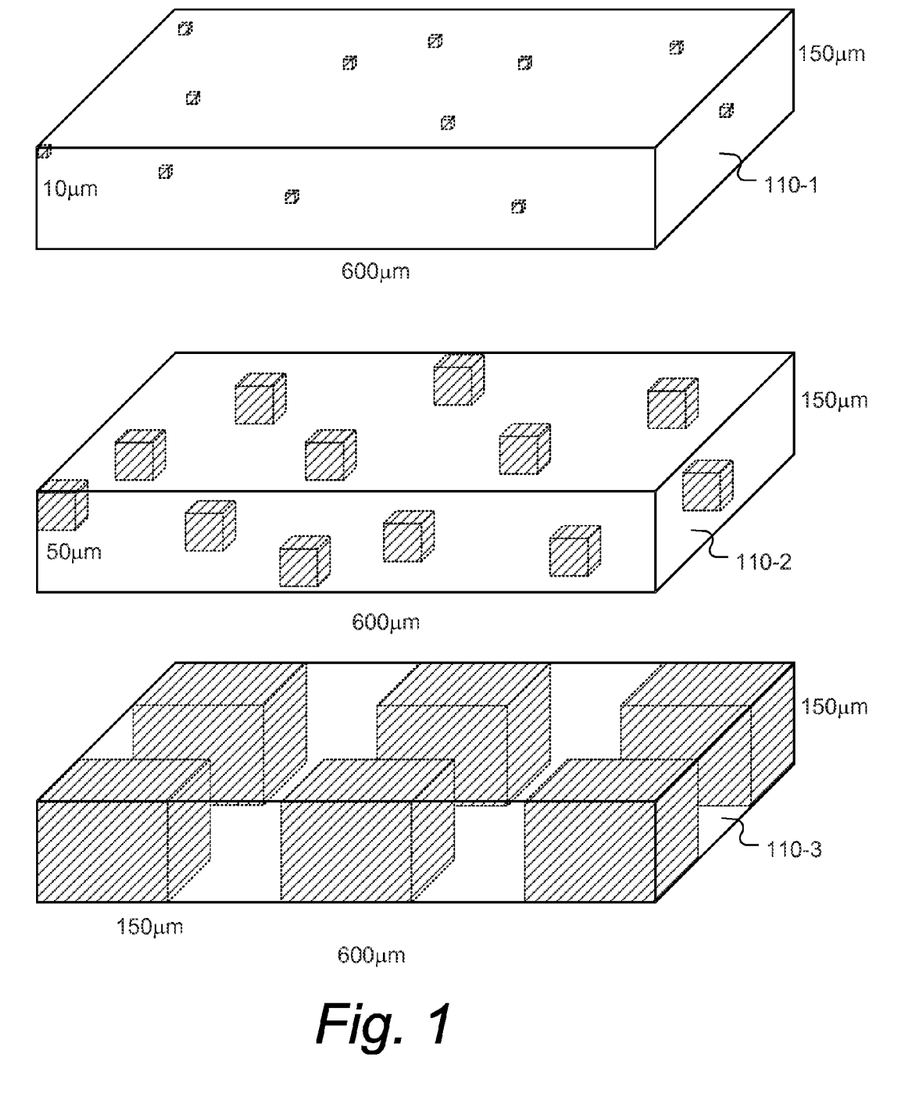
FIG. 1 illustrates a porosity representative element volume (REV), according to some embodiments.

In order to determine REV for a rock property such as porosity, one could model a large volume, subsample that volume and compute variance in porosity as a function of subsample volume. Within limitations of available computing power, multi-point statistics (MPS) can generate models of any size and shape. Because of this, MPS models can be used to help compute REVs. FIG. 1 illustrates a porosity representative element volume (REV), according to some embodiments. A pore-scale modeled volume of 600×600μ in area, 150μ in thickness is shown. The same volume can be divided into smaller sub-volumes of different sizes. For example, modeled volume 110-1 is shown with 10 μm cubes extracted, modeled volume 110-2 is shown with 50 μm cubes extracted, and modeled volume 110-3 is shown with 150 μm cubes extracted. In each case the porosities of the sub-volumes could be determined. Sub-volumes, regardless of scale, should be independent, non-overlapping volumes. If porosity variance is less than a chosen cutoff, for example +/−5%, then that volume can be used as the REV. For the purpose of flow modeling, the REV yields representative results. The generalized approach for REV determination for any rock property is, according to some embodiments: (1) model a large block with rock properties of interest; (2) randomly select a subsample of a given small size within the block; (3) randomly select another non-overlapping subsample of the same size; (4) repeat this process many times; (5) increase subsample size, and sample many similar objects; (6) plot rock property vs. subsample size, to see how variance decreases as a function of subsample size; and (7) when variance is within acceptable limits (for example, ±5%), this is the REV for the rock-property under study.

It has been found that representative element volume is an important, yet often overlooked concept. Frequently, laboratory experimentalists assume samples on which they perform measurements are representative without stating it explicitly. As a consequence, the measurements obtained from small samples are directly used for field applications either by static or dynamic modeling. This most likely leads to erroneous and misleading results due to property differences caused by sample sizes.

According to some embodiments, an integrated workflow is described to image, process, and generate physical pore models using 2D and 3D LSFM (laser scanning fluorescence microscopy). LSFM is much better than thin sections for detection and quantification of microporosity. Pores imaged by LSFM are as small as about 0.25 microns in size.

Figure 2:
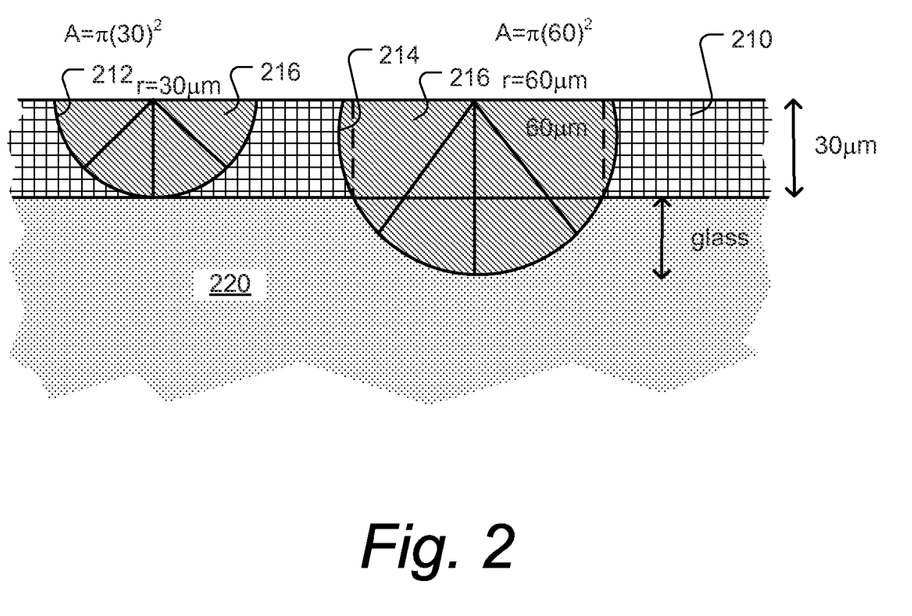
FIG. 2 illustrates a cross section view of a schematic thin section of rock having two pores and impregnated with epoxy and mounted on glass, according to some embodiments

FIG. 2 illustrates a cross section view of a schematic thin section of rock 210 having two pores 212 and 214 impregnated with epoxy 216 and mounted on glass 220, according to some embodiments. Thin sections are about 30-microns thick, and they are viewed using a microscope with transmitted light from below the stage. If a 30-micron radius (r) spherical pore 212 is bisected by the top surface of the thin section, the edge of the pore will be unclear. If a 60-micron radius spherical pore 214 is bisected by the top surface of the thin section, the pore will appear smaller (dashed lines) than its actual size. As can be seen, pores smaller than 30-microns in radius are either invisible or poorly imaged when viewed using conventional microscopy.

Further, according to some embodiments, a computation is described for representative element volumes (REVs) and areas (REAs) from non-overlapping sub-volumes or sub-areas in porous media. REVs and REAs of 3D and 2D LSFM scans, respectively, are herein used to segment lower-resolution CT scans. This helps solve a long-standing segmentation problem in rocks with pores smaller than the resolution of the CT scan images.

According to some embodiments, REVs and REAs of 3D and 2D LSFM scans, respectively, are herein used as training images for MPS (multi-point statistics) simulations, conditioned to segmented lower-resolution CT scans.

Digital rock models can be constructed from 2D thin sections, scanning-electron microscope (SEM) images, or computer-generated sphere packs. In addition, laser scanning fluorescent microscope (LSFM) images can be used to generate high-resolution (about 0.25 micron) 3D digital models. Most commonly, computed tomography (CT) scans are used to create such models: (a) conventional CT scans use relatively large samples (commonly 10-cm diameter cylindrical cores), with resolutions that are about 1 to several millimeters in size, (b) micro CT scans use small samples (commonly 5-mm diameter core plugs), with resolutions that are about 1 to 5 microns in size; synchrotron-computed microtomography works at similar scales, and (c) nano CT scans use very small samples (commonly 60-micron diameter core plugs) to detect pore bodies with resolutions that are about 50 nm to 60 nm in size.

After segmentation, according to some embodiments, software converts images to pore models. Resulting pore-body and pore-throat size distributions and pore connectivity is used to compute petrophysical properties, such as porosity and permeability. Segmentation is an image-analysis step used to generate binary images, wherein pores are differentiated from minerals. Ideally, scans are large enough to be representative element areas (REAs) or volumes (REVs), i.e., the smallest areas or volumes that can be modeled to yield consistent results, within acceptable limits of variance of the modeled property, for example, porosity or permeability.

According to some embodiments, multi-point statistics (MPS) are used to create simulations of spatial geological and reservoir property fields for reservoir modeling. These methods are conditional simulations that use known results, such as those measured in wellbores or rock samples, as fixed or "hard" data that are honored during simulations. MPS uses 1D, 2D, or 3D "training images" as quantitative templates to model subsurface property fields.

According to some embodiments, digital images of pore systems acquired by LSFM are used as training images, once an REA or REV has been sampled. LSFM images are segmented using core-plug porosity. Micro- and macropores are differentiated in LSFM scans by applying clustering, watershedding, or similar algorithms, with a size cutoff. CT scan segmentation is done using macropores identified from LSFM scans. Binarized CT scans are used as hard data in MPS simulations. Such realizations capture porosity at fine and coarse scales, and are suitable for pore-network modeling and flow simulation. This approach combines the strengths of LSFM, i.e., high resolution, with the strengths of CT scans, i.e., relatively large volumes scanned at lower resolution. Such composite models provide a "total porosity" solution.

According to some embodiments, laser scanning fluorescence microscopy (LSFM) is used to scan one or more 2D planes through rock samples impregnated with fluorescing epoxy. After confirmation of imaging of a 2D representative element area (REA) or 3D volume (REV), pore models are constructed from the scans. Segmentation is done to match laboratory-determined core-plug porosity. Clustering, watershedding or other algorithms differentiate micro- vs. macroporosity. The amount of macroporosity is used to segment micro CT scan images, which have resolutions that are too poor to resolve microporosity. LSFM scans are used as training images and segmented CT scans are used as hard data for multi-point statistical (MPS) models. The final result is a composite rock model with coarse and fine porosity.

FIG. 3 is a flow chart for a composite 2D model using laser scanning fluorescence microscopy (LSFM), microCT scans, multi-point statistics (MPS), and representative element areas (REAs), according to some embodiments. In block 310, a rock sample is vacuum-pressure impregnated with fluorescing epoxy. The clean, dry rock sample is subjected to a vacuum (for example, 12.8 psi; 0.88 bar), and epoxy is introduced that has been stained with fluorescent dye (for example, Rhodamine B, 1.5 to 200 mixture), and the combined sample and epoxy are subjected to high pressure (for example, 1,200 psi; 82.7 bar). This ensures impregnation of even the smallest connected pores. Low-viscosity, slow-curing epoxy is recommended. The sample is mounted on a glass slide, cut to the appropriate thickness, for example, a thin section is 30 microns, and a thick section is about 5,000 microns in thickness. The top surface of the rock sample is then polished.

In block 312, thin or thick sections are scanned using LSFM. Tiled 2D LSFM scans in the top 10 to 20 microns (carbonate rocks) or 50 to 250 microns (sandstones) are acquired of the thin or thick section.

Figure 4:
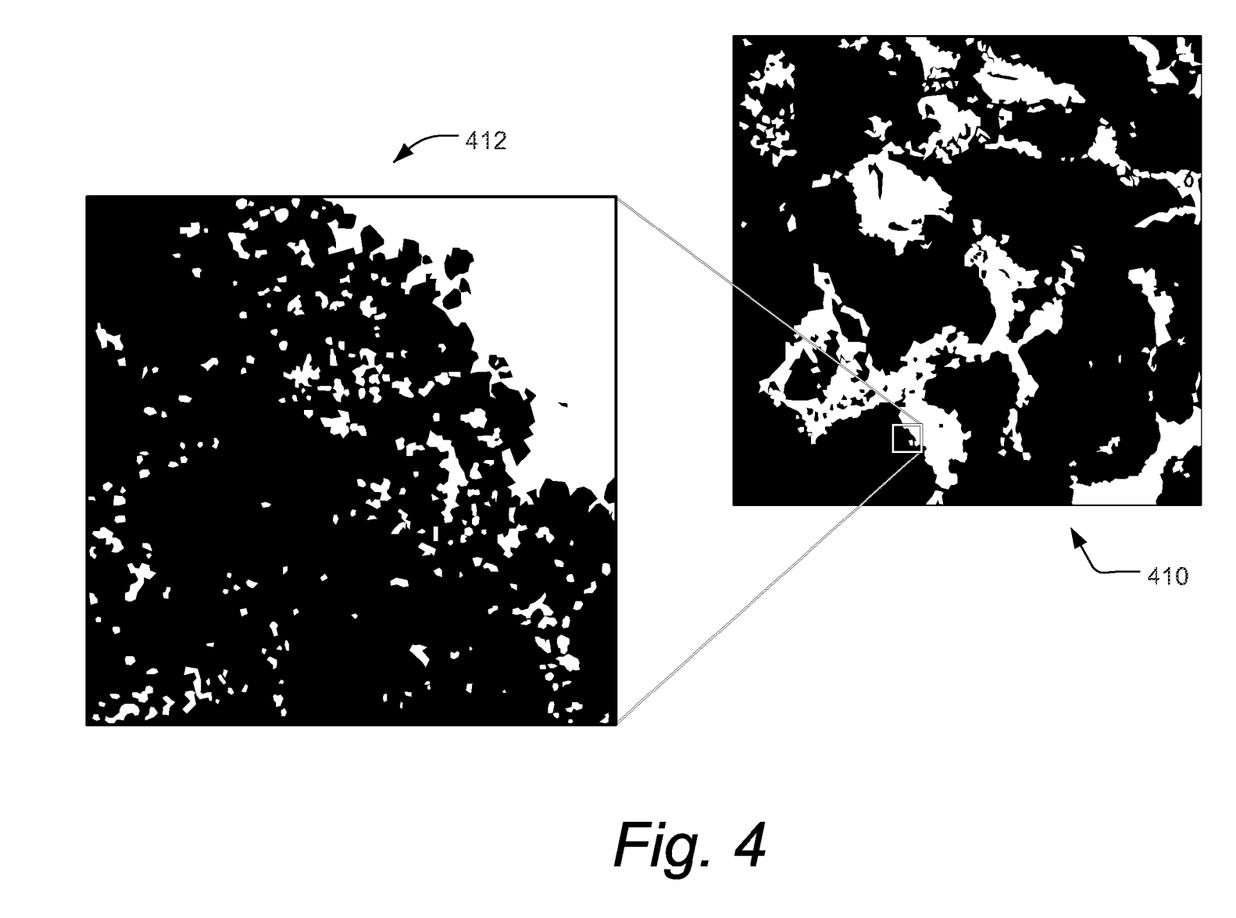
FIG. 4 illustrates a LSFM (confocal) scan of a porous rock, according to some embodiments.

FIG. 4 illustrates a LSFM (confocal) scan of a porous rock, according to some embodiments. Mineral matrix is dark, and porosity is shown in white. The entire thin section is 12,600 microns square, and frame 410 shows a 400 tile section that is 1,800 microns square. A single tile 412 is shown that is 135 microns square. The single tile illustrates an enlarged view of microporosity from high resolution confocal microscopy.

It is important to ensure the sample is level, i.e., perpendicular to the laser beam. The section, for example, is scanned using about 0.25×0.25 micron x-y steps, at a depth 5 or 10 microns below the top surface to avoid surface irregularities. The LSFM scans are saved as, for example, tif files.

Referring again to FIG. 3, in block 314, LSFM images are created and segmented. According to some embodiments, image analysis software (for example, ImageJ or Photoshop) is used to photomerge LSFM tiles. The images are segmented by choosing a threshold to match measured porosity in the corresponding core plug.

In block 316, a confirmation is made that a "representative element area (REA)" has been scanned. Porosity is computed for sub-areas of the segmented LSFM scan, and this process is repeated many times for increasing sizes of independent, non-overlapping sub-areas. Calculations are stopped when there are fewer than 30 non-overlapping sub-areas, to provide better statistics for standard-deviation calculations. Cross plots of variance in porosity vs. size of sub-area are then made. REA is the sub-area that occurs where one standard deviation of variance is within +/−5% of the sample mean (core-plug porosity). If the sample is not large enough to capture the REA, new data should be acquired for a larger sample.

In block 318, the amount of micro vs. macroporosity is calculated from the LSFM scan. 2D clustering, watershedding or a similar algorithm is used to separate touching pores. The area percent of macro- and microporosity is computed. Microporosity can be defined, for example, as pores smaller than an arbitrary cutoff, or smaller than the resolution limit of the low-resolution data.

In block 320, the thick section is imaged using micro CT scans. Micro CT scans are acquired of the thick section of rock previously used for LSFM work. Processing techniques are applied, such as filtering and smoothing, to minimize or eliminate image artifacts.

In block 322, micro CT scans are segmented using cutoff determined from LSFM for macroporosity. The amount of macroporosity determined from LSFM in block 318 is used to segment the micro CT scan volume. This process helps solve the problem of how to segment micro CT scans. The assumption is that the area percent of pores smaller than LSFM resolution (about 0.25×0.25 microns) is negligible. Pore-size frequency plots from LSFM scans show that this is a reasonable assumption.

Figure 5:
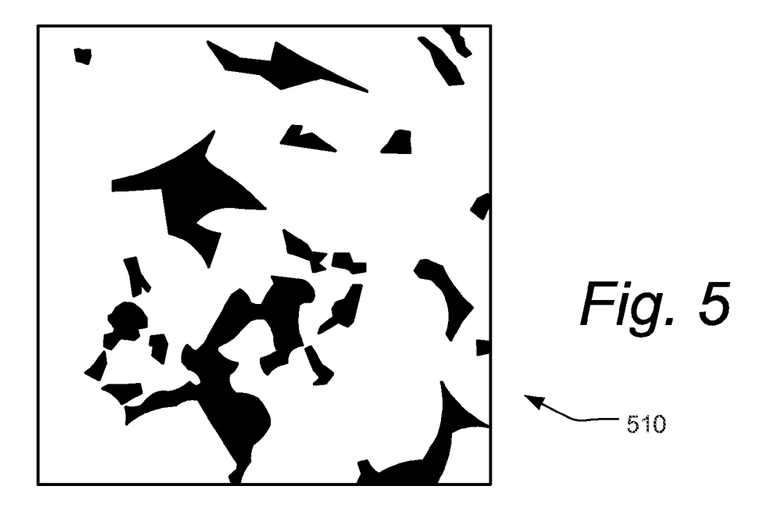
FIGS. 5 and 6 illustrate a comparison of a lower-resolution microCT scan image with higher-resolution LSFM (confocal) image of the same rock surface, according to some embodiments.
Figure 6:
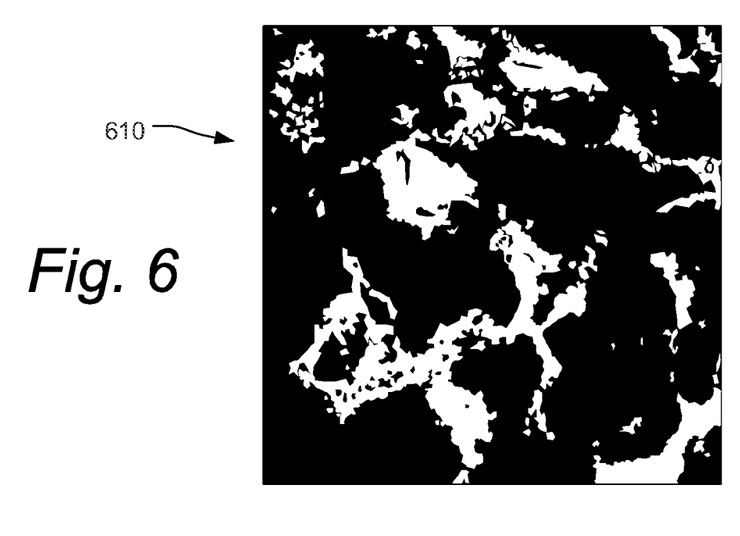

In block 324, LSFM scans are registered to micro CT scans. LSFM scans are approximately registered to micro CT scans to be certain the same portions of rock are imaged. Because LSFM scans are used as MPS (multi-point statistics) training images, exact registration is not necessary. FIGS. 5 and 6 illustrate a comparison of lower-resolution microCT scan image 510 in FIG. 5, with higher-resolution LSFM (confocal) image 610 in FIG. 6 of the same rock surface. Pores are dark and mineral matrix is light in the microCT scan image 510. Pores are light and mineral matrix is dark in the LSFM (confocal) image 610.

Referring again to FIG. 3, in block 326, micropores are replaced with null values in the LSFM scans, according to some embodiments.

In block 328, edited LSFM scans are used as training images for MPS modeling. Micro CT scan slices are resampled to match LSFM resolution, for example, about 0.25× 0.25 micron pixels. MPS modeling is run using edited LSFM scans (block 314) as training images. Resampled, segmented micro CT scan slices (block 322) are used as hard data to build the "total porosity" solution. The result is that 2D micro CT scan slices are populated with macro- and microporosity. 3D volumes can be visualized using conventional image analysis software (for example, ImageJ or Photoshop).

To deal with computer memory limitations in resampled micro CT scans, one approach is to use a novel data structure wherein MPS builds sub-models in sequence, and seamless transitions occur between sub-models using region conditioning concepts. See "Zhang, T. 2008, Incorporating geological conceptual models and interpretations into reservoir modeling using multi-point geostatistics: Earth Science Frontiers, v. 15, No. 1, p. 26-35." Sub-models are swapped from hard disk to RAM, according to the display window the user wants to see (zoom in/zoom out).

Figure 7:
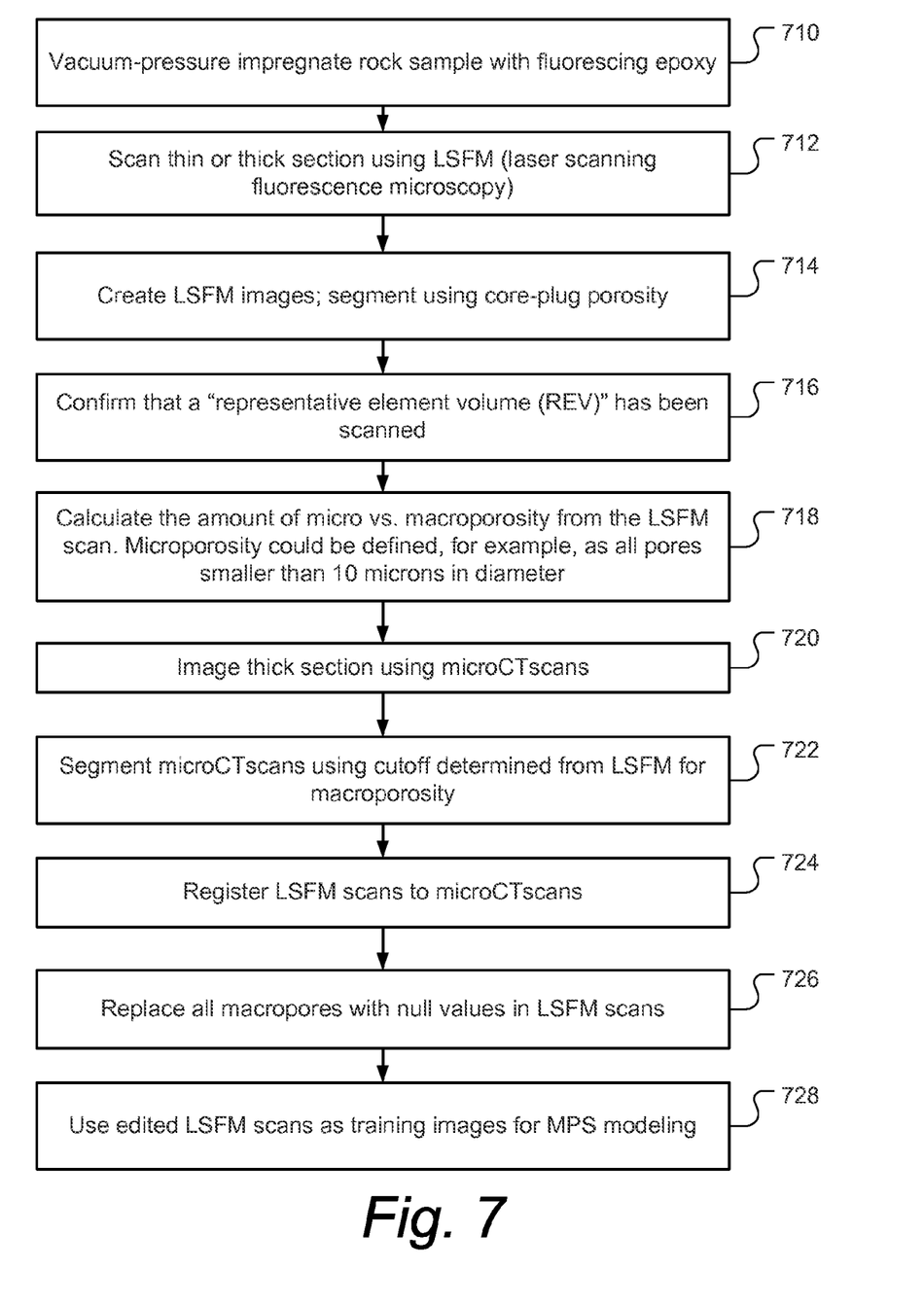
FIG. 7 is a flow chart for a composite 3D model using laser scanning fluorescence microscopy (LSFM), microCT scans, multi-point statistics (MPS), and representative element volumes (REV's), according to some embodiments.

FIG. 7 is a flow chart for composite 3D model using laser scanning fluorescence microscopy (LSFM), microCT scans, multi-point statistics (MPS), and representative element volumes (REV's), according to some embodiments. In block 710, a rock sample is vacuum-pressure impregnated with fluorescing epoxy. The clean, dry rock sample is subjected to a vacuum (for example, 12.8 psi; 0.88 bar), and epoxy is introduced that has been stained with fluorescent dye (for example, Rhodamine B, 1.5 to 200 mixture), and the combined sample and epoxy are subjected to high pressure (for example, 1,200 psi; 82.7 bar). This ensures impregnation of even the smallest connected pores. Low-viscosity, slow-curing epoxy is recommended. Mount the sample on a glass slide, cut to the appropriate thickness, for example, a thin section is 30 microns, and a thick section is about 5,000 microns in thickness. Polish the top surface of the rock sample.

In block 712, thin or thick sections are scanned using LSFM. Tiled z-stacked 3D LSFM scans in the top 10 to 20 microns (carbonate rocks) or 50 to 250 microns (sandstones) are acquired of the thin or thick section (See, FIG. 4). Care should be taken that the sample is level, i.e., perpendicular to the laser beam. The section is scanned, for example, using about 0.25×0.25 micron x-y steps, and z-steps of 0.4 microns. LSFM scans are saved as, for example, tif files.

In block 714, LSFM images are created and segmented. According to some embodiments, image analysis software (for example, ImageJ or Photoshop) is used to photomerge LSFM tiles. Segment the images by choosing a threshold to match measured porosity in the corresponding core plug. LSFM scans are visualized using image analysis software.

In block 716 a confirmation is made that a "representative element volume (REV)" has been scanned. Porosity is computed for sub-volumes of the segmented LSFM scan, and this process is repeated many times for increasing sizes of independent, non-overlapping sub-volumes. Calculations are halted when there are fewer than 30 non-overlapping sub-volumes, to provide better statistics for standard-deviation calculations. Cross plots of variance in porosity vs. size of sub-volume are then made. REV is the sub-volume that occurs where one standard deviation of variance is within +/−5% of the sample mean (core-plug porosity). If the sample is not large enough to capture the REV, new data is acquired for a larger sample.

In block 718, the amount of micro vs. macroporosity is calculated from the LSFM scan. 3D clustering, watershedding or a similar algorithm is used to separate touching pores. The volume percent of macro- and microporosity is computed. Microporosity could be defined, for example, as pores smaller than an arbitrary cutoff, or smaller than the resolution limit of the low-resolution data.

In block 720, the thick section is imaged using micro CT scans. Micro CT scans are acquired of the thick section of rock previously used for LSFM work. Processing techniques are applied, such as filtering and smoothing, to minimize or eliminate image artifacts.

In block 722, micro CT scans are segmented using the cutoff determined from LSFM for macroporosity. The amount of macroporosity determined from LSFM in block 718 is used to segment the micro CT scan volume. This process helps solve the problem of how to segment micro CT scans. The assumption is that the volume percent of pores smaller than LSFM resolution (about 0.25×0.25×0.4 microns) is negligible. Pore-size frequency plots from LSFM scans show that this is a reasonable assumption.

Figure 8:
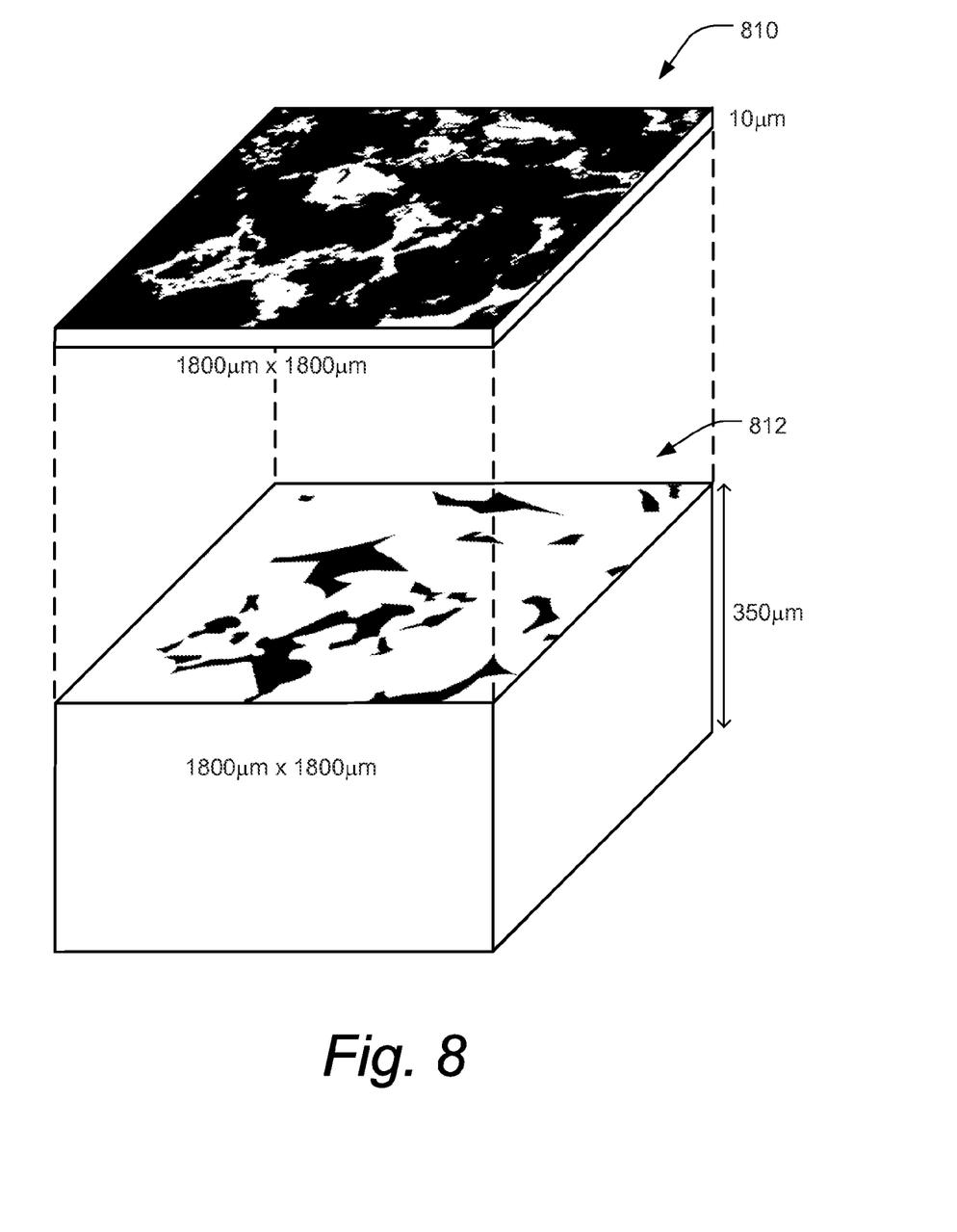
FIG. 8 illustrates registration of a confocal scan and a microCT scan of the same rock volume, according to some embodiments.

In block 724, LSFM scans are registered to micro CT scans. LSFM scans are approximately registered to micro CT scans to be certain the same portions of rock are imaged (FIG. 8). Because LSFM scans are used as MPS (multi-point statistics) training images, exact registration is not necessary.

In block 726, micropores are replaced with null values in the LSFM scans, according to some embodiments.

In block 728, edited LSFM scans are used as training images for MPS modeling. Micro CT scan slices are resampled to match LSFM resolution, for example, about 0.25× 0.25×0.4 micron pixels. MPS modeling is run using edited LSFM scans (block 714) as training images. Resampled, segmented micro CT scan slices (block 722) are used as hard data to build the "total porosity" solution.

FIG. 8 illustrates registration of a confocal scan and a microCT scan of the same rock volume, according to some embodiments. In the confocal scan 810, porosity is light, and mineral grains are dark. Voxel size is about 0.25 microns. In the micro CT scan 812, porosity is dark and mineral grains are white/light gray. Voxel size is 7 microns. Both scans 810 and 812 cover portions of the same rock volume. Scans are registered by dashed lines. The high-resolution confocal scan 810 is used as a training image for multi-point statistics simulation of porosity in the low-resolution micro CT scan 812. Sizes of scanned volumes are arbitrary.

Referring again to block 728 of FIG. 7, the result is that the micro CT scan volume is populated with macro- and microporosity. 3D volumes can be visualized using conventional image analysis software (for example, ImageJ or Photoshop).

To deal with computer memory limitations in resampled micro CT scans, one approach is to use a novel data structure wherein MPS builds sub-models in sequence, and seamless transitions occur between sub-models using region conditioning concepts. See "Zhang, T. 2008, Incorporating geological conceptual models and interpretations into reservoir modeling using multi-point geostatistics: Earth Science Frontiers, v. 15, No. 1, p. 26-35." Sub-models are swapped from hard disk to RAM, according to the display window the user wants to see (zoom in/zoom out).

Figure 9:
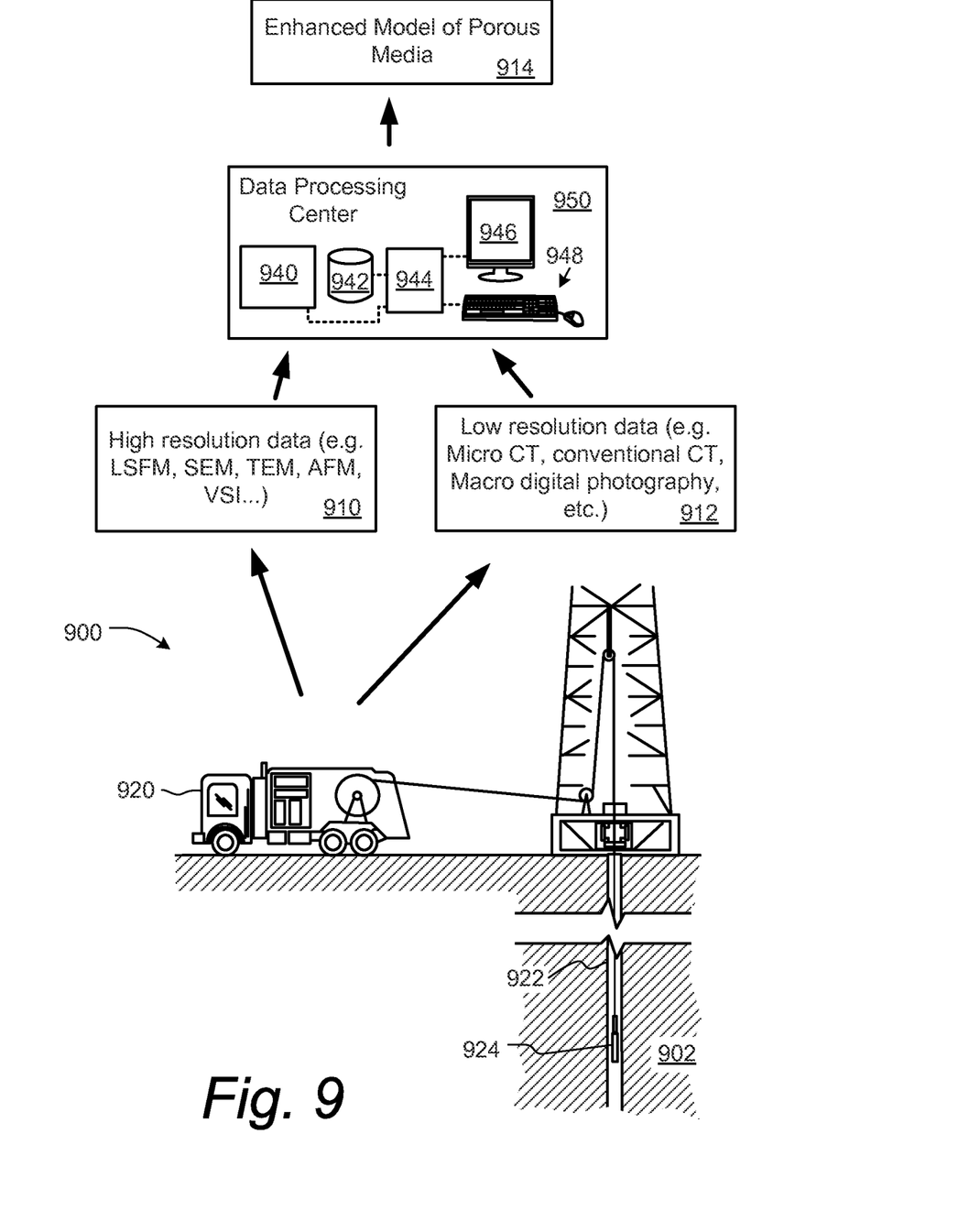
FIG. 9 shows systems for constructing an enhanced model of a sample of porous media, according to some embodiments.

FIG. 9 shows systems for constructing an enhanced model of a sample of porous media, according to some embodiments. Acquired high resolution data 910 (such as from LSFM, SEM, TEM, AFM, VSI, etc.) are transmitted to a processing center 950 which includes one or more central processing units 944 for carrying out the data processing procedures as described herein, as well as other processing. The processing center includes a storage system 942, communications and input/output modules 940, a user display 946 and a user input system 948. According to some embodiments, the processing center 950 may be located in a location remote from the acquisition site of the petrographic data. Low resolution data 912, such as acquired using micro CT, conventional CT and/or macro digital photography, are transmitted to processing center 950. In FIG. 9 data and/or samples from a subterranean porous formation 902 is being gathered at wellsite 900 via a wireline truck 920 deploying a wireline tool 924 in well 922. According to some embodiments, wireline tool 924 includes a core-sampling tool to gather one or more core samples from the porous formation 902. As described herein the data processing center is used to enhance the model 914 of the sampled porous material. Although the system in FIG. 9 is shown applied to the example of digital rock images of a subterranean porous formation, in general the described techniques can be applied to any porous media.

While the subject disclosure is described through the above embodiments, it will be understood by those of ordinary skill in the art that modification to and variation of the illustrated embodiments may be made without departing from the inventive concepts herein disclosed. Moreover, while the preferred embodiments are described in connection with various illustrative structures, one skilled in the art will recognize that the system may be embodied using a variety of specific structures. Accordingly, the subject disclosure should not be viewed as limited except by the scope and spirit of the appended claims.

What is claimed is:

1. A computer implemented method of constructing a model of a sample of porous media, the method comprising:
   receiving into a processing system a low resolution image data generated using a lower resolution measurement performed on a first sample of the porous media;
   receiving into the processing system high resolution image data representing characterizations of aspects of a small second sample of the porous media, the high resolution data being generated using a higher resolution measurement performed on the small second sample; and
   using the processing system to distribute the characterizations of aspects of the small second sample from the high resolution data into the low resolution data thereby generating an enhanced model of the porous media.

2. A method according to claim 1 wherein the small second sample forms a subset of the first sample.

3. A method according to claim 1 wherein the higher resolution measurement achieves a resolution of at least 0.5 microns.

4. A method according to claim 1 wherein the lower resolution measurement achieves a resolution of at least one order of magnitude worse than the high resolution measurement.

5. A method according to claim 1 wherein distributing includes using a multi-point statistical method.

6. A method according to claim 5 wherein the multi-point statistical method includes using one or more techniques selected from a group consisting of: discrete variable geostatistics, and continuous variable geostatistics.

7. A method according to claim 6 further comprising building a plurality of sub-models in sequence having seamless transitions using region conditioning concepts of the multi-point statistical method.

8. A method according to claim 1 wherein the characterizations of aspects of the small second sample of the porous media include characterizations of one or more aspects selected from a group consisting of: shape, size and spacing of pores.

9. A method according to claim 1 wherein the porous media is a subterranean rock formation.

10. A method according to claim 9 wherein the porous media is a hydrocarbon bearing reservoir rock formation.

11. A method according to claim 1 further comprising prior to the distributing, segmenting the low resolution image data into a binary image, the segmentation being based in part on the characterizations from high resolution measurement.

12. A method according to claim 1 wherein the high resolution image data is generated using one or more measurements selected from a group consisting of: laser scanning fluorescent microscopy, scanning electron microscopy, transmission electron microscopy, atomic force microscopy, vertical-scanning interferometry, nanoCTscans, and focused ion beam-scanning electron microscopy.

13. A method according to claim 12 wherein the high resolution image data is generated using one or more measurements selected from a group consisting of: two dimensional thin section, two dimensional thick section, and two dimensional transmitted laser scanning fluorescence microscopy.

14. A method according to claim 1 wherein the low resolution image data is generated using one or more measurements selected from a group consisting of: three dimensional micro CT, three dimensional conventional CT and three dimensional synchrotron CT scans, and macro digital photography.

15. A method according to claim 1 wherein the high resolution image data is two-dimensional, the low resolution image data is three-dimensional, and the model is three-dimensional.

16. A method according to claim 1 further comprising determining a representative element area (REA) size that is smaller than the small second sample using an iterative process, whereby variance in porosity or permeability is measured for successively larger sample areas.

17. A method according to claim 16 further comprising prior to the distributing, segmenting the low resolution image data into a binary image, the segmentation being performed so as to match macroporosity computed for an REA.

18. A method according to claim 1 further comprising determining a representative element volume (REV) size that is smaller than the small second sample using an iterative process, whereby variance in porosity or permeability is measured for successively larger sample volumes.

19. A method according to claim 18 further comprising prior to the distributing, segmenting the low resolution image data into a binary image, the segmentation being performed so as to match macroporosity computed for an REV.

20. A system for constructing a model of a sample of porous media, the system comprising a processing system adapted and programmed to receive low resolution image data generated using a lower resolution measurement performed on a first sample of the porous media, receive high resolution image data representing characterizations of aspects of a small sample of the porous media, the high resolution data being generated using a higher resolution measurement performed on the small second sample, and to distribute the characterizations of aspects of the small second sample from the high resolution data into the low resolution data thereby generating an enhanced model of the porous media.

21. A system according to claim 20 wherein the distributing includes using a multi-point statistical method.

22. A system according to claim 20 wherein the characterizations of aspects of the small second sample of the porous media include characterizations of one or more aspects selected from a group consisting of: shape, size and spacing of pores.

23. A system according to claim 20 wherein the porous media is a subterranean rock formation.

24. A system according to claim 23 wherein the porous media is a hydrocarbon bearing reservoir rock formation.

25. A system according to claim 24 further comprising a sampling system adapted to collect a core-sample from the subterranean rock formation.

26. A system according to claim 20 wherein the processing system is further programmed to segment the low resolution image data into a binary image, the segmentation being based in part of the characterizations from high resolution measurement.

27. A system according to claim 20 further comprising a high resolution imaging system adapted to generate the high resolution image data using one or more measurements selected from a group consisting of: laser scanning fluorescent microscopy, scanning electron microscopy, transmission electron microscopy, atomic force microscopy, vertical-scanning interferometry, nano CT, and focused ion beam-scanning electron microscopy.

28. A computer implemented method of segmenting a digital image of porous media, the method comprising:
  receiving into a processing system a low resolution digital image generated using a lower resolution measurement performed on a first sample of the porous media;
  receiving into a processing system a high resolution digital image generated using a higher resolution measurement performed on a small second sample of the porous media;
  using the processing system to identify macropores from the high resolution digital image; and
  using the processing system to segment the low resolution digital image thereby generating a binary digital image having two possible values for each pixel, the segmenting being based on the identified macropores.

29. A method according to claim 28 further comprising:
  characterizing aspects of the small second sample from the high resolution digital image; and
  distributing the characterizations into the low resolution digital image thereby generating an enhanced model of the porous media.

30. A method according to claim 29 wherein distributing includes using a multi-point statistical method.

31. A method according to claim 30 wherein the multi-point statistical method includes using one or more techniques selected from a group consisting of discrete variable geostatistics, and continuous variable geostatistics.

32. A method according to claim 28 wherein the porous media is a hydrocarbon bearing subterranean rock formation.

* * * * *